United States Patent
Deka et al.

[11] Patent Number: 5,909,278
[45] Date of Patent: Jun. 1, 1999

[54] TIME-RESOLVED FLUORESCENCE DECAY MEASUREMENTS FOR FLOWING PARTICLES

[75] Inventors: Chiranjit Deka, Miami, Fla.; John A. Steinkamp, Los Alamos, N.M.

[73] Assignee: The Regents of the University of California, Los Alamos, N.M.

[21] Appl. No.: 08/902,395

[22] Filed: Jul. 29, 1997

Related U.S. Application Data

[60] Provisional application No. 60/022,767, Jul. 29, 1996.
[51] Int. Cl.$^6$ .............................. G01J 3/30; G01N 21/64; G01N 21/76
[52] U.S. Cl. .................. 356/318; 250/461.1; 250/461.2; 436/172; 356/73
[58] Field of Search ..................................... 356/318, 445, 356/446, 73; 250/461.1, 461.2; 436/172, 523, 524, 525, 526, 528, 531, 534, 805, 808

[56] References Cited

U.S. PATENT DOCUMENTS

| | | | |
|---|---|---|---|
| 4,573,796 | 3/1986 | Martin et al. | 356/318 |
| 5,260,764 | 11/1993 | Fukuda et al. | 356/73 |
| 5,317,162 | 5/1994 | Pinsky et al. | 250/461.2 |
| 5,504,337 | 4/1996 | Lakowixz et al. | 250/461.2 |

OTHER PUBLICATIONS

A. Castro et al., "Fluorescence Detection And Size Measurement Of Single DNA Molecules," Analytical Chemistry 65, 849–852 (1993).

M.A. Condrau et al., "Time–Resolved Flow Cytometer For The Measurement Of Lanthanide Chelate Fluorescence: I. Concept And Theoretical Evaluation," Cytometry 16, 187–194 (1994).

M.A. Condrau et al., "Time–Resolved Flow Cytometer For The Measurement Of Lanthanide Chelate Fluorescence: II. Instrument Design And Experimental Results," Cytometry 16, 195–205 (1994).

C. Deka et al., "Simultaneous Dual–Frequency Phase–Sensitive Flow Cytometric Measurements for Rapid Identification of Heterogeneous Fluorescence Decays in Fluorochrome–Labeled Cells and Particles," Cytometry 21, 318–328 (1995).

C. Deka et al., "Time–Resolved Fluorescence–Decay Measurement and Analysis on Single Cells by Flow Cytometry," Appl. Opt. 35, 4481–4489 (Aug. 1, 1996).

*Primary Examiner*—Frank G. Font
*Assistant Examiner*—Zandra V. Smith
*Attorney, Agent, or Firm*—Samuel M. Freund

[57] ABSTRACT

Time-resolved fluorescence decay measurements for flowing particles. An apparatus and method for the measurement and analysis of fluorescence for individual cells and particles in flow are described, wherein the rapid measurement capabilities of flow cytometry and the robust measurement and analysis procedures of time-domain fluorescence lifetime spectroscopy are combined. A pulse-modulated cw laser is employed for excitation of the particles. The characteristics and the repetition rate of the excitation pulses can be readily adjusted to accommodate for fluorescence decays having a wide range of lifetimes.

21 Claims, 7 Drawing Sheets

TIME-RESOLVED FLUORESCENCE DECAY MEASUREMENTS FOR FLOWING PARTICLES

This application claims the benefit of U.S. Provisional application No. 60/022,767, filed on Jul. 29, 1996.

The present invention relates generally to fluorescence decay measurements and, more particularly, to the measurement of the time-resolved fluorescence decay for flowing particles excited by suitable light sources. This invention was made with government support under Contract No. W-7405-ENG-36 awarded by the U.S. Department of Energy to The Regents of the University of California. The government has certain rights in the invention.

FIELD OF THE INVENTION

BACKGROUND OF THE INVENTION

Rapid measurements of fluorescence from individual cells by flow cytometry allows large samples of cells, organisms and subcellular components to be statistically analyzed in a short period of time. See, e.g., *Flow Cytometry and Sorting*, $2^{nd}$ edition, M. R. Melamed, T. Lindmo, and M. L. Mendelsohn eds., Wiley-Liss, N.Y., 1990. For flow cytometric analysis, the cells are stained with fluorescent probes that bind to a specific subcellular component. The fluorescence intensity from these probes, upon excitation by a continuous wave light source, gives a measure of the particular subcellular component in the cell. Flow cytometric measurements find application in a wide range of biological areas such as cell biology (See, e.g., "Cytochemical Techniques For Multivariate Analysis Of DNA And Other Cellular Constituents," by H. A. Crissman and J. A. Steinkamp, in *Flow Cytometry And Sorting*, $2^{nd}$ edition, M. R. Melamed, T. Lindmo, and M. L. Mendelsohn eds., Wiley-Liss, N.Y., 1990, pages 227–248, and "Quantitative Cell Cycle Analysis," by J. W. Gray, F. Dolbeare, and M. G. Pallavicini, in *Flow Cytometry And Sorting*, $2^{nd}$ edition, M. R. Melamed, T. Lindmo, and M. L. Mendelsohn eds., Wiley-Liss, N. Y., 1990, pages 44514 468.), chromosome analysis and sorting (See, e.g., "Flow Karyotyping And Chromosome Sorting," by J. W. Gray and L. S. Cram in *Flow Cytometry And Sorting*, $2^{nd}$ edition, M. R. Melamed, T. Lindmo, and M. L. Mendelsohn eds., Wiley-Liss, N.Y., 1990, pages 50314 530.), immunology (See, e.g., "Immunofluorescence Techniques," by M. R. Loken, in *Flow Cytometry And Sorting*, $2^{nd}$ edition, M. R. Melamed, T. Lindmo, and M. L. Mendelsohn eds., Wiley-Liss, N.Y., 1990, pages 341–353.), hematology (See, e.g., "Analysis And Sorting Of Blood And Bone Marrow Cells," by J. W. M. Visser in *Flow Cytometry And Sorting*, $2^{nd}$ edition, M. R. Melamed, T. Lindmo, and M. L. Mendelsohn eds., Wiley-Liss, N.Y., 1990, pages 669–684.), and microbiology (See, e.g., "Application Of Flow Cytometry On Bacteria: Cell Cycle Kinetic, Drug Effects And Quantitation Of Antibody Binding," by H. B. Steen et al., Cytometry 2, 249–257 (1982).).

Recent advances in fluorescence lifetime spectroscopy have shown that the study of fluorescence decay and excited state lifetimes can provide valuable information on subcellular organization, the fluorescence decay of the probes being sensitive to the surrounding microenvironment. See, e.g., *Principles Of Fluorescence Spectroscopy*, by J. R. Lakowicz, Plenum Press, New York, 1983, and *Mechanisms Of Energy Transfer: In Biophysics*, W. Hoppe, W. Lohmann, H. Markl, and H. Ziegler eds., Springer Verlag, Berlin, 1983. Fluorescence decay can provide insight into intermolecular interactions at the subcellular level, which are often accompanied by changes in the fluorescence decay of the molecules involved. See, e.g., "Mechanism of Fluorescence Concentration Quenching of Carboxyfluorescein in Liposomes-Energy Transfer to Non-Fluorescent Dimers," by R. F. Chen et al., Anal. Biochem. 172, 61–77 (1988). As a result, it is important to know if any change in the characteristic of the fluorescence decay or the fluorescence lifetime has occurred in a system under investigation. A flow cytometric method that permits detailed time-resolved analysis of fluorescence decays in single cells, is not available. Such analysis by flow cytometry is expected to have many advantages over similar measurements in bulk solution or suspensions in a cuvette (See, e.g., "Fluorescence Lifetime Analysis of DNA Intercalated Ethidium Bromide and Quenching by Free Dye," by D. P. Heller et al., Biophys. Chem. 50, 305–312 (1994) and "Analysis of Fluorescence Quenching in Some Antioxidants from Nonlinear Stern-Volmer Plots," by H. Zeng et al., J. Luminescence 63, 75–84 (1995)), which is another method by which fluorescence decay studies in biological samples are conducted. For example, experiments in a cuvette provide only an average measure for the fluorescence properties of the collection of all the cells contained in the sample. See e.g., D. P. Heller, supra, and "Nanosecond Fluorescence Microscopy," by S. M. Keating et al., Biophys. J. 59, 186–202 (1991). Additionally, since the illumination volume in such measurements is relatively large, the interference from the background signals (fluorescence from unbound dye, Raman scattering from the medium of suspension, etc.) can be significant. A microscope-based system permits analysis of individual cells on a slide. See, S. M. Keating, supra, and "Development of a Streak-Camera Based Time-Resolved Microscope Fluorimeter and Its Application to Studies of Membrane Fusion in Single Cells," by A. Kusumi et al., Biochem. 30, 6517–6527 (1991). However, the speed at which the cells can be studied is slow because each cell must be brought into the illumination region manually. By contrast, however, in a flow cytometer not only is each cell sampled and measured individually, but the rate of sampling is high. Hundreds of cells can be measured per second in a flow cytometer. Since the cells pass through the laser beam in single file, no further adjustments are required from cell to cell, once the flow cytometer is properly aligned. See, e.g., "Flow Cytometer for Resolving Signals From Heterogeneous Fluorescence Emissions and Quantifying Lifetime in Fluorochrome Labeled Cells and Particles by Phase-Sensitive Detection," Rev. Sci. Instrum. 64, 3440–3450 (1993), and "Fluorescence Lifetime Measurements in a Flow Cytometer by Amplitude Demodulation Using Digital Data Acquisition Technique," by C. Deka et al., Cytometry 17, 94–101, (1994). Further, for the fluorescence decay measurements using a microscope, a synchronously pumped cavity dumped dye laser was used (S. M. Keating, supra), with the pump laser being a mode-locked argon-ion laser. By contrast, laser-based flow cytometers use cw lasers for most conventional applications. See, e.g., Melamed, Crissman, Gray, Loken, Visser, and Steen, supra. By using an electrooptic modulator (EOM) it should be possible to conveniently adapt a cw laser for pulsed time-resolved fluorescence decay measurements instead of using an expensive and complicated multilaser, cavity-dumped system.

Measurements of apparent fluorescence lifetimes in single cells have been made in flow cytometers by frequency domain spectroscopy (See, e.g., Lakowicz, supra, and "Phase-Sensitive Fluorescence Spectroscopy: A New Method to Resolve Fluorescence Lifetimes and Emission Spectra of Components in a Mixture of Fluorophores," J. R.

Lakowicz et al., J. Biochem. Biophys. Methods. 5, 19–35 (1981)) using a cw laser sinusoidally modulated at a single modulation frequency. See, also., Lakowicz, supra, and "Phase-Resolved Fluorescence Lifetime Measurements for Flow Cytometry," P. G. Pinsky et al., Cytometry 14, 123–135 (1993). In this method, an apparent lifetime is measured from the phase-shift of the fluorescence signal relative to the modulated excitation at the given modulation frequency. This apparent lifetime gives a true measure of the intrinsic fluorescence lifetime if the fluorescence decay is exponential. A phase shift measured at a single modulation frequency, however, cannot, by itself, determine if a particular decay is exponential in form. Moreover, the lifetimes calculated from the measured phase shifts for multiexponential or nonexponential decays depend on the modulation frequency. See, e.g., J. R. Lakowicz et al., "Picosecond Resolution of Tryosime Fluorescence and Anisotropy Decays by 2 GHz Frequency-Domain Fluorometry," by J. R. Lakowicz et al., Biochem. 26, 82–90 (1987), and "Measuring Fluorescence Decay Times by Phase-Shift and Modulation Using the High Harmonic Content of Pulsed Light Sources," by E. Gratton et al., Nuovo Cimento B15, 110–124 (1980). As a result, a single frequency measurement is not sufficient for the analysis of fluorescence decays that do not follow a single exponential law. It is known that in a system where intermolecular interactions between neighboring fluorochromes lead to nonradiative energy transfer and energy migration, the fluorescence decay becomes nonexponential. See, e.g., J. R. Lakowicz, Dorr, and Chen, supra. In addition, nonexponential decays in flow cytometry can also result simply from the fact that the cells are often labeled with multiple probes having different lifetimes. Therefore, an alternative method is required that permits detailed analysis of arbitrary fluorescence decays from individual cells and particles in flow. Time-domain lifetime spectroscopy offers a convenient solution to this problem. In this situation, if the fluorescence intensity due to a pulsed excitation is measured as a function of time and the system's response function is deconvoluted from the recorded fluorescence data, the impulse response function of the fluorescence decay can be extracted for any arbitrary decay law. See, e.g., J. R. Lakowicz; "Deconvolution of Fluorescence and Phosphorescence Decay Curves-Least Squares Method," by W. R. Ware et al., J. Phys. Chem. 77, 2038–2048 (1973); "Correction of Instrumental Time Response Variation with Wavelength in Fluorescence Lifetime Determinations in the Ultraviolet Region," by D. M. Reyner et al., Rev. Sci. Instrum. 48, 1050–1054 (1977); "On the Analysis of Fluorescence Decay Kinetics by the Method of Least Squares," by A. Grinvald et al., Anal. Biochem. 59, 583 (1974); and "Data Reduction and Error Analysis for the Physical Sciences," by P. R. Bevington, McGraw-Hill, New York, 1969. Time-resolved measurements have been reported for flowing streams of dilute solutions of dye molecules. See, e.g., "Detection and Lifetime Measurement of Single Molecules in Flowing Sample Streams by Laser-Induced Fluorescence," by C. W. Wilkerson et al., App. Phys. Lett. 62(17), 2030–2032 (1993) and "Error Analysis of Simple Algorithms for Determining Fluorescence Lifetimes of Ultradilute Dye Solutions," by S. A. Soper et al., Appl. Spectro. 48, 400–405 (1994). These measurements were made by the gated single-photon counting technique using mode-locked lasers at high repetition rates (76 MHz –82 MHz, pulse-to-pulse period 13.2 ns–12.2 ns), and have been concerned with fluorescence decays having lifetimes of the order of 4 ns or less. The analyses were based on the assumption of a single exponential decay. Due to the high repetition rate of the laser in such systems, however, one could not analyze fluorescence decays having lifetimes longer than one third of the repetition time period of the laser pulses, particularly, if the decay were nonexponential. Further, the duration of the data acquisition for these measurements ranged from 3 ms (Wilkerson, supra) to 10 s (Soper, supra). For flow cytometric analysis of biological cells, however, the data for each cell must be acquired within its transit time across the laser beam. Typically, this is on the order of 20 $\mu$s. See, e.g., Steinkamp and Deka, supra. Further, in order to be of practical use for biological studies, the measurement and analysis method must be general enough to include both exponential and nonexponential decays. Finally, it must permit analysis of fluorescence decays having lifetimes up to as long as 25 ns (Heller, supra) or longer. Moreover, since the conventional laser-based flow cytometers already use a cw laser for excitation, it would be advantageous and less expensive if the lifetime sensing method could be adapted to use a cw laser.

In "Fluorescence Detection And Size Measurement Of Single DNA Molecules," by Alonso Castro et al., Analytical Chemistry 65, 849–852 (1993), fluorescence in flowing molecules is detected. However, a time-gate window is employed so that only delayed fluorescence is detected. For investigation of nonexponential decay, it is necessary to observe the characteristics of the fluorescence early in the decay curve. In "Time-Resolved Flow Cytometer For The Measurement Of Lanthanide Chelate Fluorescence: I. Concept And Theoretical Evaluation," by Marc A. Condrau et al., Cytometry 16, 187–194 (1994) and in "Time-Resolved Flow Cytometer For The Measurement Of Lanthanide Chelate Fluorescence: II. Instrument Design And Experimental Results," by Marc A. Condrau et al., Cytometry 16, 195–205 (1994), the authors also discuss the measurement of delayed luminescence.

Accordingly, it is an object of the present invention to perform time-resolved fluorescence decay measurements on single particles in flow.

Another object of the invention is to perform time-domain measurements of the fluorescence decay of fluorochrome-labeled single flowing particles that can be adapted to a conventional flow cytometer (using a cw laser), can readily accommodate a wide range of lifetimes, and can be applied to both exponential and nonexponential decays.

Yet another object of the present invention is to perform time-resolved fluorescence decay measurements on single particles in flow in order to extract the complete decay law governing the fluorochromes in the particles.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus for measuring time-resolved fluorescence decay for flowing particles containing a plurality of fluorochromes of this invention includes: means for generating a train of light pulses having a known temporal relationship therebetween, each of the light pulses having a wavelength suitable for exciting particles containing fluorochromes; a first detector for receiving and detecting individual light pulses and producing a first electrical signal in response thereto; means for providing a flow of particles through the train of light pulses, whereby individual particles may interact with the light pulses producing fluorescence light for particles containing fluorochromes and scattered light for particles without fluorochromes; means for separating scattered light from fluorescence light; a second detector for receiving and detecting light emitted from the interaction of the particles with the light pulses and producing a second electrical signal in response thereto; and means, triggered by the second electrical signal, for receiving and storing the first electrical signal and the second electrical signal; whereby the commencement time for the first electrical signal corresponding to a second electrical signal from the detection of scattered light from particles without fluorochromes and the first electrical signal corresponding to a second electrical signal from the detection of fluorescence from fluorochrome-containing particles are used to correct the commencement time of the second electrical signal for fluorescence from fluorochrome-containing particles, and a response function for said apparatus is generated and used to extract the time-resolved fluorescence decay from the fluorescence emission of the fluorochrome-containing particles.

In another aspect of the present invention and in accordance with its objects and purposes, the method for measuring time-resolved fluorescence decay for flowing particles containing a plurality of fluorochromes of this invention includes the steps of: generating a train of light pulses having a known temporal relationship therebetween, each of the light pulses having a wavelength suitable for exciting particles containing fluorochromes; detecting individual light pulses and producing a first electrical signal in response thereto; providing a flow of particles through the train of light pulses, whereby individual particles may interact with the light pulses producing fluorescence light for particles containing fluorochromes and scattered light for particles without fluorochromes; separating scattered light from fluorescence light; detecting light emitted from the interaction of the particles with the light pulses and producing a second electrical signal in response thereto; receiving and storing the first electrical signal and the second electrical signal; whereby the commencement time for the first electrical signal corresponding to a second electrical signal from the detection of scattered light from particles without fluorochromes and the commencement time for the first electrical signal corresponding to a second electrical signal from the fluorescence of fluorochrome-containing particles are used to correct the commencement time of the second electrical signal for fluorescence from fluorochrome-containing particles; and determining the response function for said step of detecting scattered light emitted from the interaction of the particles with the light pulses; whereby the time-resolved fluorescence decay may be extracted by deconvoluting the response function for the fluorescence emission of the fluorochrome-containing particles.

Benefits and advantages of the present invention include the performance of time-domain measurements of the fluorescence decay of fluorochrome-labeled single cells that can be adapted to a conventional flow cytometer (by use of a cw laser), can readily accommodate a wide range of lifetimes, and can be applied to both exponential and nonexponential decays.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION

Briefly, the present invention includes an apparatus and method for the measurement and analysis of fluorescence of individual cells and particles in flow. It combines the rapid measurement capabilities of a flow cytometer and the robust measurement and analysis procedures of time-domain fluorescence lifetime spectroscopy. A pulse modulated cw laser is employed for excitation of the particles.

The characteristics and the repetition rate of the excitation pulses can be readily adjusted to accommodate for fluorescence decays having a wide range of lifetimes. The method permits time-resolved fluorescence decay measurements on single cells in a flow cytometer using optical pulses from an electrooptically modulated (EOM) cw laser. The pulse repetition rate is easily adjusted by varying the repetition rate of the electrical pulse generator used to drive the electrooptic modulator, EOM. The option to conveniently change the repetition rate of the excitation pulses permits the measurement time-window to be adjusted to accommodate for fluorescence decays having long lifetimes. By deconvoluting the system response function from the measured fluorescence pulse, the impulse response function can be extracted for both exponential and nonexponential decays. The trigger for the data acquisition system is activated by the entry of a )o particle (e.g., a cell) into the illumination volume, using the fluorescence (or the scatter) signal from the particle as the trigger. This allows recording of the data only when a particle passes through the laser beam. The analytical procedure for deconvoluting the system response function has been adapted to accommodate for this particle-activated trigger mechanism.

The present method is applied to fluorescent microspheres and to biological cells stained with different dyes. Specifically, the measurement and analysis of both single and double exponential decays is demonstrated for individual Chinese hamster ovary (line CHO) cells stained with propidium iodide (PI) only, fluorescein isothiocyanate (FITC) only, and with both PI and FITC. The system was tested using standard fluorescent microspheres with known fluorescence decay and lifetime.

Reference will now be made in detail to the present preferred embodiments of the invention, an example of which is illustrated in the accompanying drawings. For time-domain fluorescence decay measurements, the sample (i.e., a cell or a particle) is excited by a pulse of light. The true fluorescence signal due to this pulsed excitation is the convolution of the impulse response function of the fluorescence decay and the excitation light pulse. Since the measurement system itself has a finite response time, the recorded fluorescence pulse is actually the convolution of the true fluorescence signal and the instrument's response function. In other words, the measured fluorescence signal is the convolution of the fluorescence decay and the system response function, where the system response function is the convolution of the excitation light pulse and the instrument's response function. Thus, the system response function is given by $$e(t) = [L(t) \otimes S(t)], \quad (1)$$

and the recorded fluorescence signal is given by $$F(t) = e(t) \otimes D(t), \quad (2)$$

where L(t), S(t), D(t) are the temporal profile of the excitation light pulse, the instrument response function, and the impulse response function of the fluorescence decay, respectively. The symbol ⊗ represents a convolution between two functions. In an actual experiment, the system response function, e(t), is obtained by measuring the scattered signal from a nonfluorescent particle, and deconvolutes it from the measured fluorescence signal, F(t), to extract D(t). In integral notation, $$F(t) = \int_0^t D(t')e(t-t')dt'. \quad (3)$$

If the base line of the optical excitation is not zero, i.e., the transient pulses are superimposed upon a continuous wave (cw) intensity K, the system response function, represented by the scattered signal, is given by $$E(t) = K + e(t) \quad (4)$$

The measured fluorescence intensity due to the above excitation is given by $$F(t) = \int_0^t D(t')(K + e(t-t'))dt', \text{ from which} \quad (5)$$

$$F(t) = K \int_0^t D(t')dt' + \int_0^t D(t')e(t-t')dt',$$

$$F(t) = K' + \int_0^t D(t')e(t-t')dt', \text{ or}$$

$$F(t) = K' + \int_0^t D(t-t')e(t')dt'$$

The first term on the right hand side of Equation (5) represents the steady-state fluorescence due to the cw part of the excitation. The second term gives the pulsed component of the fluorescence signal and is superimposed on the cw intensity. If the respective base lines are subtracted from the scattered signal (K in Equ. 4) and the fluorescence signal (K' in Equ. 5), the baseline corrected pair of signals behave as if there was no cw excitation in the first place. Therefore, the impulse response function of the fluorescence decay can be extracted by deconvoluting the baseline corrected function, E(t)-K, from the baseline corrected fluorescence signal F(t)-K'. For digitally acquired datasets, however, the start time may have a nonzero value, say $t_R$, that marks an instant before the pulse has a chance to rise above the baseline. In that situation, the lower limit for the above integration, that gives the convolution of the decay law with the response function, should be taken as $t_R$, and a numerical integration performed accordingly. The deconvolution is accomplished by the method of Grinvald et al. Here, a model decay function $$D(t) = \sum_i \alpha_i \exp(-t/\tau_i) \quad (6)$$

is assumed and is convoluted with the measured systems response function repeatedly, each time varying the parameters ($\alpha_i$ and $\tau_i$, until the difference between the reconvoluted signal and the experimental fluorescence signal is minimized. This procedure is known as the iterative reconvolution method. It is straightforward to extend the fitting procedure to arbitrary nonexponential decay functions that may not be expressed as the sum of a finite number of exponential decays. See, e.g. Ware, supra.

Figure 1A:
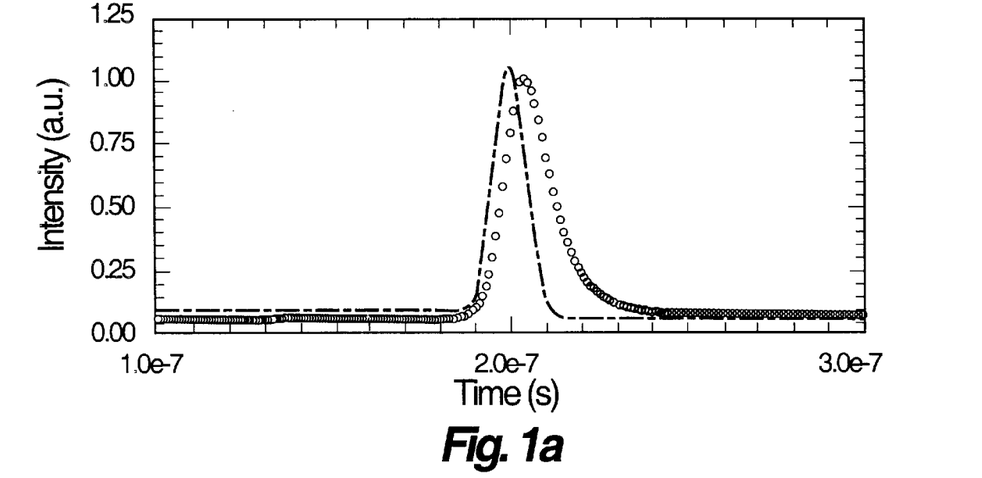
FIG. 1a shows a simulated excitation pulse (dashed curve) and a simulated fluorescence pulse (open circles) from a particle having a single exponential decay with a lifetime of 7 ns.
Figure 1B:
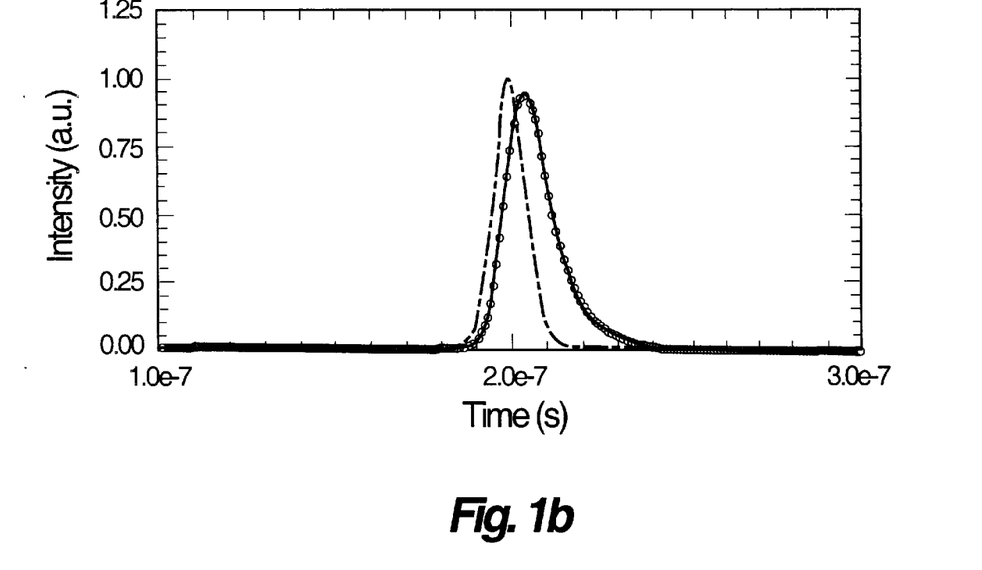
FIG. 1b shows a theoretical fit obtained by iterative-reconvolution analysis of the data in FIG. 1a after respective baselines were subtracted.

Turning now to the drawings, FIG. 1a shows a simulated excitation pulse (dashed curve) and a simulated fluorescence pulse (open circles) from a particle having a single exponential decay with a lifetime of 7 ns, while FIG. 1b shows a theoretical fit obtained by iterative-reconvolution analysis of the data in FIG. 1a after respective baselines were subtracted. The fluorescence pulse was calculated by convoluting a single exponential decay having a lifetime of 7 ns, with the excitation pulse. For clarity, only the data points at every half nanosecond interval are shown for the fluorescence signal, and the theoretical fit is shown by a solid line. The simulated excitation signal used to calculate the fluorescence signal was assumed to be a Gaussian-shaped pulse, approximately 10 ns wide (full-width-at-half-maximum), with a nonzero cw baseline, K=0.05. This closely resembles the typical optical pulses that are generated by the EOM used in the present work. The iterative reconvolution analysis was made after subtracting the respective cw baselines from the pair of excitation and fluorescence signals. The theoretical best fit to the baseline subtracted fluorescence pulse is shown by the solid line in FIG. 1b. With a starting lifetime value of 3 ns, the optimization converged in three iterations, with an optimum of 7 ns obtained in the final iteration. This verifies that the iterative reconvolution procedure can extract the true impulse-response function when applied to a pair of scattered and fluorescence signals from which the respective cw base lines have been subtracted prior to the analysis.

Figure 2:
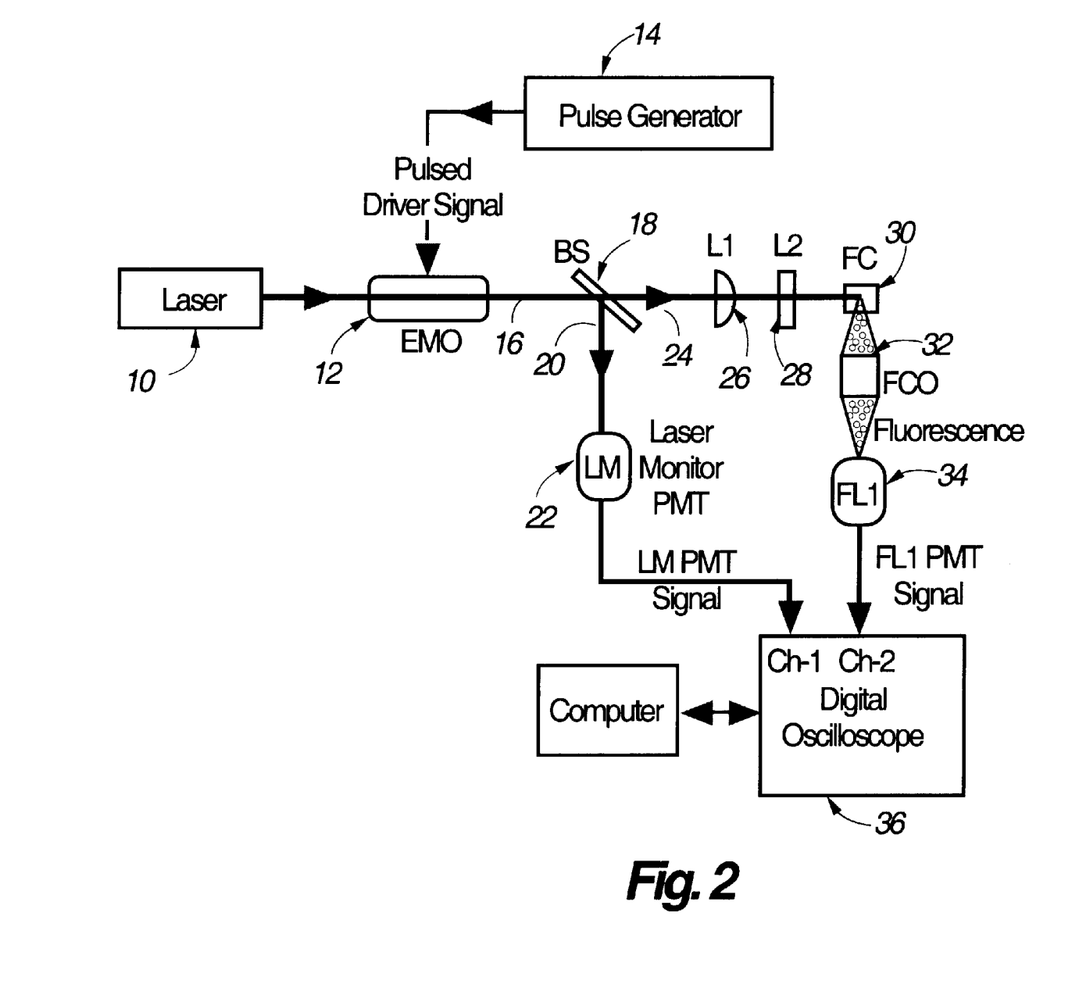
FIG. 2 is a schematic representation of the apparatus used for the fluorescence decay measurements of the present invention. Photomultiplier detector, FL1, detects both fluorescence and scattered light emitted from excited particles in flow cell, FC, collected by fluorescence collection optics, FCO, while photomultiplier detector, LM, measures laser pulses derived from electrooptic modulator, EOM, after reflection from beam splitter, BS.

FIG. 2 is a schematic representation of the flow cytometer apparatus used for the time-resolved fluorescence decay measurements of the present invention. Optical pulses at 488 nm were generated from a cw Ar-laser, 10, using EOM, 12. The EOM was driven by electrical pulse generator, 14. The pulsed laser beam, 16, from the EOM was passed through glass-wedge beamsplitter, 18, which reflected a small portion of the beam, 20, onto photomultiplier tube, PMT, LM, 22. The transmitted portion of beam, 24, was focused by crossed cylindrical lenses, L1, 26, and L2, 28, into flow chamber, FC, 30. The flow chamber was a quartz cuvette open at both ends inserted into a fluid flow line (not shown in FIG. 2). The internal cross-section of the cuvette was approximately 200 $\mu m^2$ square. A saline solution flowed through the cuvette at high pressure (approximately 6 psi), and the sample stream containing the biological cells was injected through a capillary tube along the axis of this flow. The pressurized saline solution, also called the sheath fluid, maintained the sample solution in a narrow stream-line flow along the axis of the flow chamber by hydrodynamic focusing. The direction of the flow was perpendicular to the laser beam entering the cuvette. The fluorescence signal generated by a particle passing through the focused laser beam was separated from the scattered light using a laser-line blocking color filter which is part of the fluorescence collection optics, FCO, 32, and was detected by PMT tube FL1, 34. To measure the system's response function, the scattered signal from a nonfluorescent particle was recorded by the same PMT, 34. For the scattering measurements, the color filter was replaced by appropriate neutral density filters. Due to the approximately Gaussian spatial profile of the laser beam, the pulsed cytometric signals had a Gaussian envelope. For the fluorescence decay analysis, only one pulse from each fluorescence pulse train was required. The fluorescence pulse was digitized and recorded in Channel 2 of digital signal storage oscilloscope, 36, at a sampling rate of 1 GS/sec. Simultaneously, a pulse from laser monitor 22 was also digitized and recorded in Channel 1 of oscilloscope 36. The oscilloscope was also triggered by the signal in the Channel 2. To obtain the system response function, the scattered pulse from a nonfluorescent particle was measured by PMT 34 and recorded in Channel 2, with a corresponding laser pulse from the PMT 22 recorded in the Channel 1. As will be discussed hereinbelow, the laser pulses recorded in Channel 1 are required for the proper temporal alignment of the fluorescence and the scattered pulses, for subsequent deconvolution analysis of the fluorescence signal.

The digital data acquisition system was managed efficiently by triggering the system only when a particle passed through the illumination volume. This event-activated trigger mechanism, however, resulted in different initial-time reference points for the fluorescence and the scattered signals from different particles, depending on their risetime characteristics. Therefore, prior to deconvoluting the system's response function from the measured fluorescence pulse, the initial-time reference points for the pair of signals must be corrected. Since the excitation laser pulses were generated by the EOM at a stable repetition rate, the necessary correction was obtained by directly recording a pulse from the laser beam using a second PMT (LM) for each triggered event, and measuring the apparent shift between the laser pulses. For analysis, the scattered pulse from the nonfluorescent particle was shifted by this amount prior to deconvolution. To make efficient use of the large number of fluorescence decay files rapidly acquired by the present flow cytometer, the data analysis software must combine the time-correction procedure with the iterative reconvolution program.

Instead of the pulse-modulated cw laser, a mode-locked laser can be used to make the fluorescence lifetime measurements. See, e.g., Lakowicz, supra. However, if the standard single-pulse deconvolution technique is used for the data analysis, the repetition rate of the excitation must be lowered by using either a pulse-picker or a cavity-dumped technique using a secondary laser to accommodate for fluorescence decays longer than approximately 4 ns. This is because the cw mode-locked lasers typically have repetition rates of approximately 76–82 MHz. As a result, if a particle has a lifetime longer than 4 ns, the fluorescence decays due to successive excitation pulses will overlap. In that case, the single-pulse deconvolution analysis cannot be used. The electrooptic modulation of cw lasers is advantageous because the repetition rate of the output pulses can be continuously varied over a wide range and can easily accommodate fluorescence decays having different lifetimes. This also offers an additional practical advantage because all laser-based flow cytometers already use a cw laser. As a result, the present method can be readily adapted to existing systems to make fluorescence decay measurements, as was the case for the flow cytometer used in this work.

The resolution of the measurement and analysis depends on the accuracy of the time-shift correction applied to the scatter signal. This correction factor depends on the sampling rate of the waveforms. At a sampling rate of 1 GS/sec, the resolution of the analysis is approximately 1.4 ns (i.e., ±0.7 ns). This can be decreased to less than 0.5 ns (i.e., ±0.25 ns) by sampling the waveforms at 5 GS/sec. Combining the high digitization sampling rate of commercially available instruments with the readily adjustable pulse repetition rate of the EOM, the present method can be expected to accommodate fluorescence decays having lifetimes ranging from the subnanoseconds to tens of nanoseconds. For accurate subnanosecond lifetime measurements, the pulses must be sampled at least at the rate of 200 ps per point (5 GS/sec). For fluorescent decays with long lifetimes of the order of 30 ns, on the other hand, an approximately 300 ns pulse-to-pulse separation is also required. This will provide a time window in which the fluorescence intensity of the pulse may drop by $e^{-10}$ of its peak value. That will be more than sufficient for accurate analysis of the decay using the single pulse deconvolution method. Such a window is easily created by EOM pulses adjusted to a repetition rate of less than 3.3 MHz. For the data acquisition, digital oscilloscopes having a 300 ns measurement window, and sampling at the rate of 5 GS/sec, are commonly available.

Figure 3A:
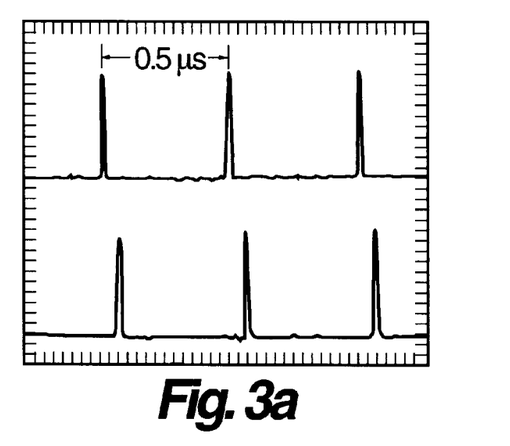
FIG. 3a is an oscilloscope trace of the electrical pulses from the pulse generator (top), and the pulsed laser output from the EOM (bottom).
Figure 3B:
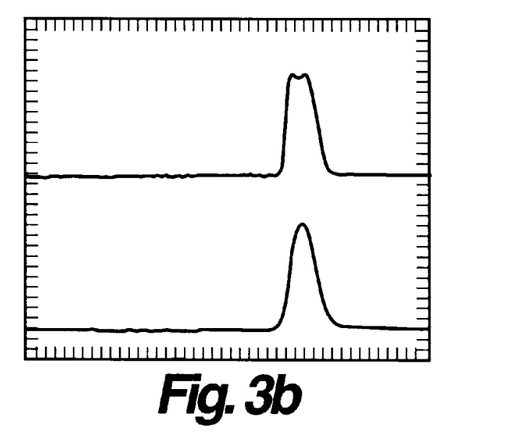
FIG. 3b shows the pulse shape of the electrical signal (top) and the laser output from the EOM (bottom).
Figure 3C:
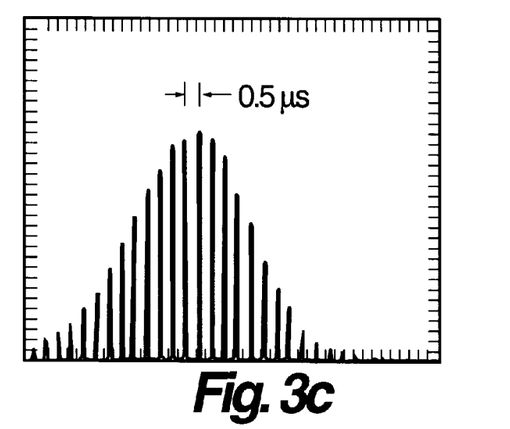
FIG. 3c shows a flow cytometer signal obtained from a nonfluorescent particle passing through the pulsed laser beam.

FIG. 3a shows typical oscilloscope traces for the electrical driver pulses (top trace) and the signal corresponding to EOM (12, in FIG. 2) output laser pulses (bottom trace). The shape of the laser pulses depends on the characteristics of the electrical driver signal, specifically, the width, rise time and fall time. In FIG. 3b, the upper trace shows a typical individual electrical pulse, and the lower trace shows the shape of an individual laser pulse when viewed in an expanded time scale. FIG. 3c shows a flow cytometric-scattered signal obtained from a nonfluorescent particle passing through the pulsed laser beam and measured by FL1 (34, in FIG. 2), as viewed in a compressed time scale. Similar pulses are also obtained for fluorescence signals from fluorescent particles.

Figure 4A:
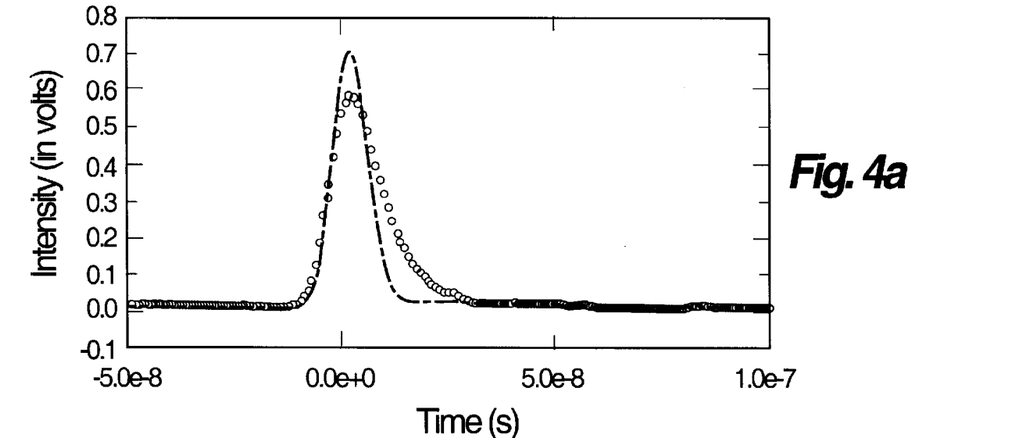
FIG. 4a shows a fluorescence pulse obtained from a microsphere (circles), and a scattered pulse from a nonfluorescent microsphere (dashed curve). Each pulse was acquired in Channel 2 of the digital oscilloscope illustrated in FIG. 2 hereof, and is overlaid in this figure for comparison. The pulse parameters of the electrical driver signal were w=10 ns, lead=1 ns, and trail=6 ns.

FIG. 4a shows a pulsed fluorescence signal (circles) from a fluorescent microsphere excited at 488 nm by the pulsed laser beam in the flow cytometer. The system response curve was measured by recording the scattered signal from a nonfluorescent microsphere (beaded line). Each trace was recorded in the Channel 2 of the oscilloscope in two separate runs, and is overlaid in this FIG. 4 for comparison.

Figure 4B:
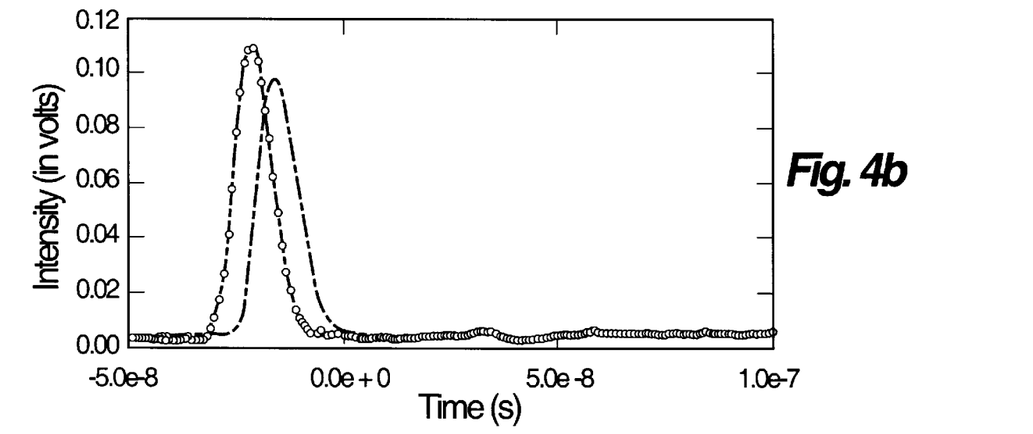
FIG. 4b shows laser pulses measured by the laser-monitor photomultiplier tube, PMT, (LM) which correspond to the scattering signal from the nonfluorescent microsphere (dashed curve) and the fluorescence signal form the fluorescent microsphere (circles), respectively.
Figure 4C:
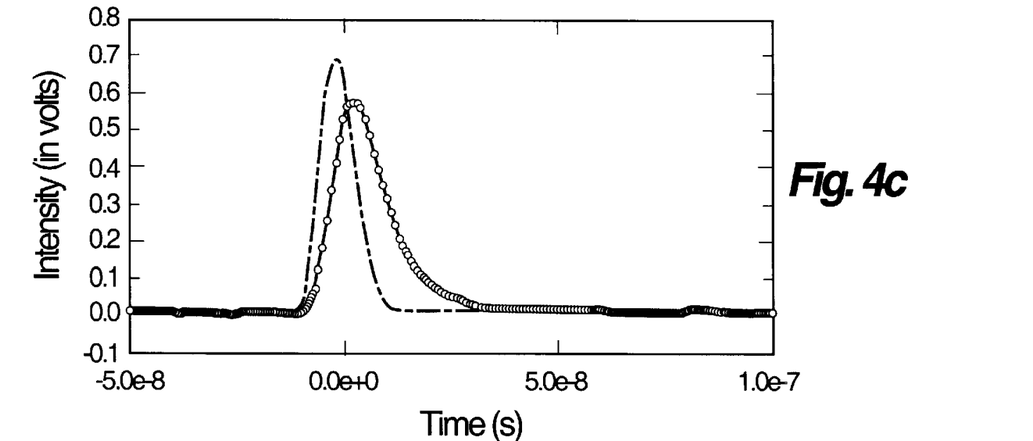
FIG. 4c shows the scatter pulse from FIG. 4a after being shifted relative to the fluorescence pulse by an amount equal to the apparent shift between the corresponding laser pulses, and corrected for the respective cw baselines. Iterative reconvolution analysis of the pair of time-corrected and baseline subtracted fluorescence and scatter signals resulted in the theoretical fit shown by the solid line passing through the fluorescence data points (circles).

In order for the deconvolution method to work, a one-to-one correspondence between digitized points of the fluorescence and the scattered pulses must be retained. The pair of pulses must be temporally aligned so that the measured fluorescence pulse truly represents a convolution of the system response function and the impulse response function of the fluorescence decay. However, if the data acquisition system is triggered by the signal from the PMT FL1 (measuring either fluorescence or the scattered pulse), as was the case in the present method, the initial reference time for each signal depends on the characteristics of its rising end. Therefore, raw data for the fluorescence signal recorded by the digital oscilloscope had an initial-time reference that was different from the initial-time reference for the scattered pulse measured subsequently from the nonfluorescent particle. As a result, the pair of fluorescence and scatter pulses could not be properly analyzed by deconvolution without first correcting for this relative shift in their respective initial-time references. The laser pulses measured directly by the laser monitor PMT (LM) served as the common references to accomplish this correction. Since the laser pulses were generated at a stable repetition rate, any relative shift observed between the laser pulses measured for the two different triggered events must be due to the trigger-time variations for the two cases. For example, FIG. 4b shows the laser pulses recorded by the laser monitor PMT (LM) corresponding to the two events shown in FIG. 4a. Each of these pulses was acquired in Channel 1 of the oscilloscope. The oscilloscope was triggered by the signal in Channel 2 thereof. By measuring the apparent relative shift between the two laser pulses, and shifting the scattered pulse with respect to the fluorescence pulse by the same amount, the pair of fluorescence and scattered pulses are aligned to the same initial-time reference. FIG. 4c shows the pair of pulses shown in FIG. 4a after the time-correction has been made. The relative positions of the two pulses after this correction reflect the expected time lag of the fluorescence signal with respect to the scattered signal due to the finite excited-state lifetimes of the fluorescent molecules. Notice that, in addition to the time correction, the respective baselines were also subtracted from this pair of signals. The impulse response function of the fluorescence decay was extracted by deconvoluting the time- and baseline corrected fluorescence signal, using the iterative reconvolution method. In FIG. 4c the solid line through the fluorescence data points (circles) is the theoretical fit obtained from this pair of time-and baseline corrected pulses. It predicted a single exponential decay with a lifetime of 6.74 ns. This is in agreement with the measurements previously made on these fluorescent particles using the frequency domain method in bulk suspension in a cuvette. See, e.g., Deka, supra.

Figure 5A:
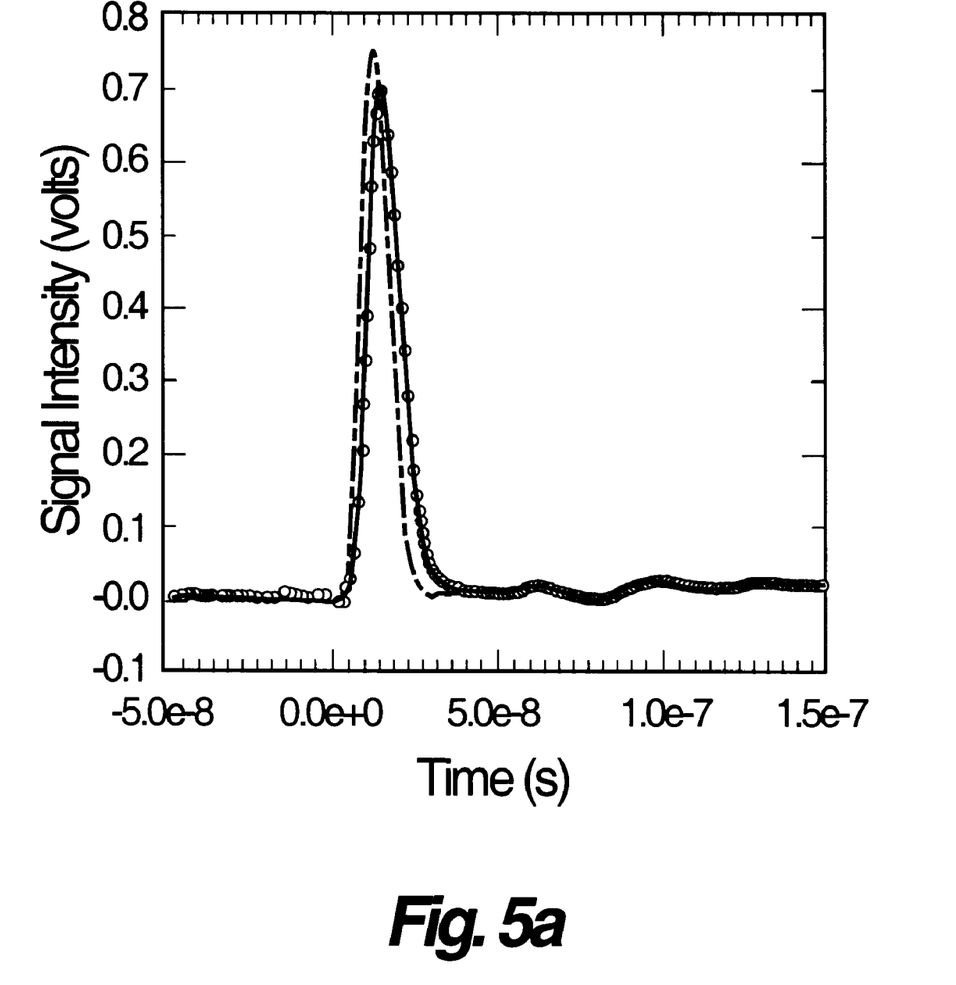
FIGS. 5a–5c show the iterative reconvolution analysis of the fluorescence signals from CHO cells stained with FITC, (a), Pi, (b), and both FITC and PI, (c). The pulse parameters of the electrical driver signal for the EOM were w=10 ns, lead=1 ns, and trail=6 ns for FIGS. 5a and b. For measurements shown in FIG. c, the electrical driver signal parameters were w=8 ns, lead=2 ns, and trail=1 ns. For each case, a pair of fluorescence and scattered signals is shown after trigger-time and baseline corrections. The baseline-subtracted fluorescence data points are represented by the circles, the time-corrected and baseline-subtracted scatter signal is represented by the nonuniform dashed line, and the theoretical best fit obtained by the iterative reconvolution is represented by the uniform solid line.
Figure 5B:
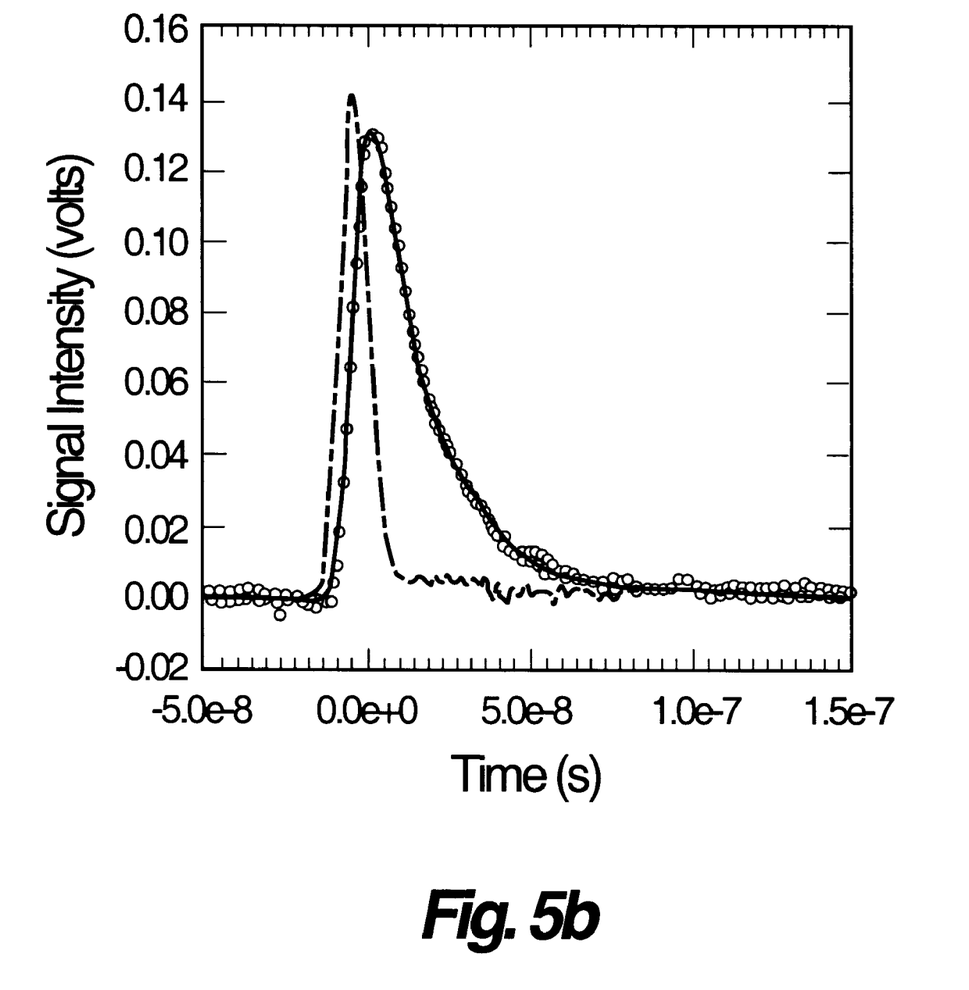
Figure 5C:
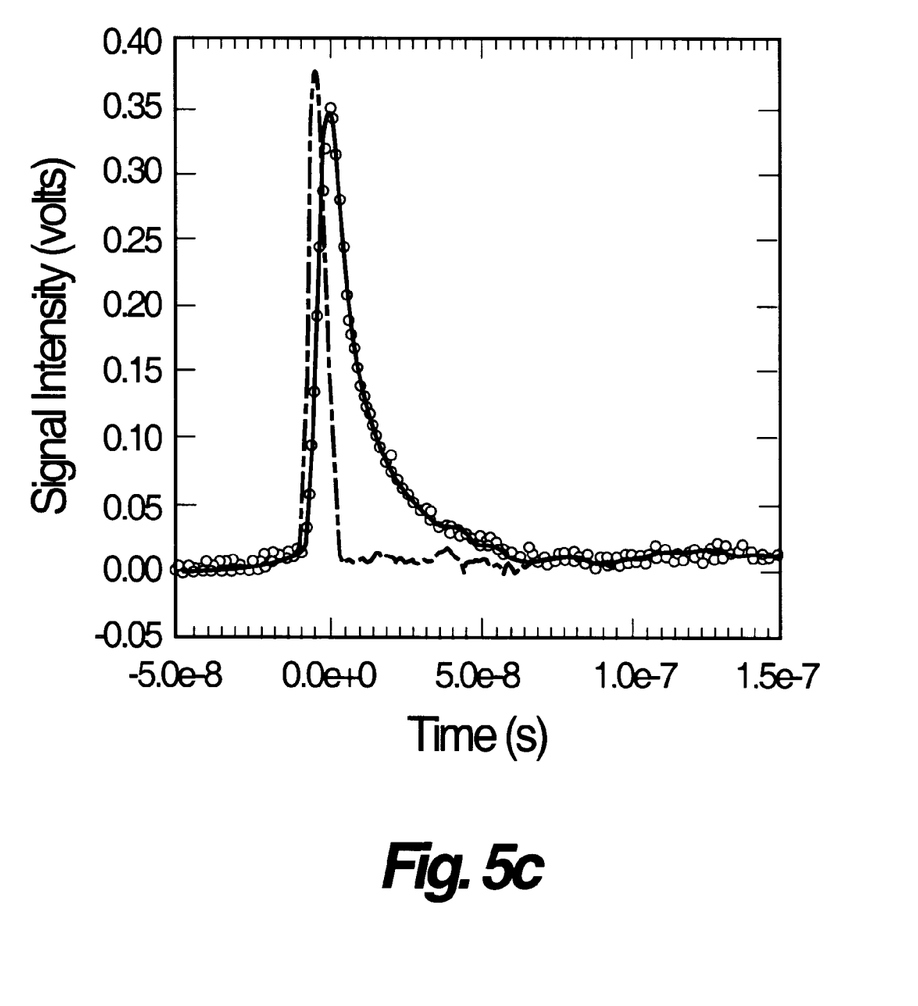

The above technique has been applied to CHO cells stained with propidium iodide (PI) and FITC, both alone as well as in combination. PI and FITC stained the DNA and the protein content of the cell respectively. For the staining, the CHO cells, were maintained in exponential growth phase in suspension culture, free of mycoplasma, in Ham's F-10 medium supplemented with heat-activated newborn calf serum (15%), penicillin (100 U/ml), and streptomycin (100 $\mu$l/ml). Cells were harvested, fixed in 70% ethanol (1 h), and centrifuged. The ethanol fixative was removed prior to staining. See, e.g., "Rapid One Step Staining Procedures for Analysis of Cellular DNA and Protein by Single and Dual Laser Flow Cytometry," H. A. Crissman et al., Cytometry 3, 84–90 (1982). To stain with FITC only, the fixed cells were treated with a solution containing 0.5 $\mu$g/ml FITC. To stain with PI alone, the cells were treated with a solution containing 1.5 $\mu$g/ml of PI. For the combined PI/FITC staining, the cells were treated with a solution containing 0.1 $\mu$g/ml FITC and 1.5 $\mu$g/ml PI. The cells were analyzed 1–2 hours after staining. FIG. 5 shows the fluorescence signals and the respective theoretical fits for three different CHO cells stained respectively with FITC only (5a), PI only (5b), and both PI and FITC (5c). The theoretical fit to the date for the FITC stained cell (FIG. 5a) predicted a single exponential decay having a lifetime of 3.4 ns. The chi-square parameter (Reyner, Grinvald, and Bevington, supra), giving the quality of the theoretical fit, was 0.03. For the PI stained cell, a single exponential decay with an estimated lifetime of 14.7 ns (FIG. fb) fitted the data. The chi-square for the fit was 0.004. These are in agreement with lifetimes of FITC and PI stained cells reported earlier using alternative methods. See, e.g., Steinkamp, supra. For the cell stained with both FITC and Pi, the theoretical fit predicted a sum of two exponential decays having lifetimes of 14.6 ns and 3.5 ns, with relative fractional intensities of approximately 76.7% and 23.3% respectively (FIG. 5c). The chi-square for the fit was 0.018.

As stated, the present invention includes a time-domain method for the measurement and analysis of fluorescence decays of fluorochrome labeled cells in flow. Excitation pulses are generated by electrooptically modulating a cw laser. The system response function is then obtained by measuring the scattered signal from a nonfluorescent particle, and deconvoluted from the fluorescence signal by an iterative reconvolution method. Excitation pulses as wide as 10 ns were used to analyze single-exponential and double-exponential decays having lifetimes ranging from approximately 3.5 ns to 15 ns.

Application of electrooptically modulated pulses from a cw laser for fluorescence decay measurement and analysis of single cells by flow cytometry has been demonstrated. Both single and double exponential fluorescence decays having lifetimes in the range of 3 ns to 15 ns have been measured. The resolution of the measurement at 1 GS/sec sampling rate is approximately 1.4 ns (i.e., ±0.7 ns). This can be decreased to less than 0.5 ns by sampling the waveforms at 5 GS/sec.

The foregoing description of the invention has been presented for purposes of illustration and description and is not intended to be exhaustive or to limit the invention to the precise form disclosed, and obviously many modifications and variations are possible in light of the above teaching. For example, it would be apparent to one having ordinary skill in the art of fluorescence measurements, after carefully reviewing the present disclosure, that electrically modulated diodes and electrically modulated diode-pumped lasers can be employed as excitation sources.

The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for measuring time-resolved fluorescence decay for flowing particles containing a plurality of fluorochromes, which comprises in combination:
   (a) means for generating a train of light pulses having a known temporal relationship therebetween, each of the light pulses having a wavelength suitable for exciting particles containing fluorochromes;
   (b) a first detector for receiving and detecting individual light pulses and producing a first electrical signal in response thereto;
   (c) means for providing a flow of particles through the train of light pulses, whereby individual particles may interact with the light pulses producing fluorescence light for particles containing fluorochromes and scattered light for particles without fluorochromes;
   (d) means for separating scattered light from fluorescence light;
   (e) a second detector for receiving and detecting light emitted from the interaction of the particles with the light pulses and producing a second electrical signal in response thereto; and
   (f) means, triggered by the second electrical signal, for receiving and storing the first electrical signal and the second electrical signal; whereby the commencement time for the first electrical signal corresponding to a second electrical signal from the detection of scattered light from particles without fluorochromes and the first electrical signal corresponding to a second electrical signal from the detection of fluorescence from fluorochrome-containing particles are used to correct the commencement time of the second electrical signal for fluorescence from fluorochrome-containing particles, and a response function for said apparatus may be generated and used for extracting the time-resolved fluorescence decay from the fluorescence emission of the fluorochrome-containing particles.

2. The apparatus for measuring time-resolved fluorescence decay for flowing particles containing a plurality of fluorochromes as described in claim 1, wherein said means for providing a flow of particles includes hydrodynamically focused particle flow.

3. The apparatus for measuring time-resolved fluorescence decay for flowing particles containing a plurality of fluorochromes as described in claim 2, wherein the hydrodynamically focused particle flow is provided by a flow cytometer.

4. The apparatus for measuring time-resolved fluorescence decay for flowing particles containing a plurality of fluorochromes as described in claim 1, wherein said means for generating a train of light pulses is selected from the group consisting of electrooptic modulated cw lasers and acoustooptic modulated cw lasers.

5. The apparatus for measuring time-resolved fluorescence decay for flowing particles containing a plurality of fluorochromes as described in claim 1, wherein said means for separating fluorescent light from scattered light includes optical filters.

6. The apparatus for measuring time-resolved fluorescence decay for flowing particles containing a plurality of fluorochromes as described in claim 1, wherein said means for generating a train of light pulses includes mode-locked lasers having means for lowering the pulse repetition rate thereof such that the time between pulses is at least three times longer than the fluorescence decay lifetime of the fluorochrome-containing particles.

7. The apparatus for measuring time-resolved fluorescence decay for flowing particles containing a plurality of fluorochromes as described in claim 1, wherein said means for generating a train of light pulses is selected from the group consisting of electrically modulated diode lasers and electrically modulated diode pumped lasers.

8. The apparatus for measuring time-resolved fluorescence decay for flowing particles containing a plurality of fluorochromes as described in claim 1, wherein the light pulses having a known temporal relationship therebetween are equally spaced in time.

9. The apparatus for measuring time-resolved fluorescence decay for flowing particles containing a plurality of fluorochromes as described in claim 8, wherein the light pulses having a known temporal relationship therebetween have a chosen pulse repetition rate and pulsewidth.

10. The apparatus for measuring time-resolved fluorescence decay for flowing particles containing a plurality of fluorochromes as described in claim 9, wherein the light pulses having a known temporal relationship therebetween have a pulse repetition rate such that the time between pulses is at least three times longer than the fluorescence decay lifetime of the fluorochrome-containing particles.

11. The apparatus for measuring time-resolved fluorescence decay for flowing particles containing a plurality of fluorochromes as described in claim 1, wherein said means for receiving and storing the first electrical signal and the second electrical signal is a digital storage oscilloscope.

12. A method for measuring time-resolved fluorescence decay for flowing particles containing a plurality of fluorochromes, which comprises the steps of:
   (a) generating a train of light pulses having a known temporal relationship therebetween, each of the light pulses having a wavelength suitable for exciting particles containing fluorochromes;
   (b) detecting individual light pulses and producing a first electrical signal in response thereto;
   (c) providing a flow of particles through the train of light pulses, whereby individual particles may interact with the light pulses producing fluorescence light for particles containing fluorochromes and scattered light for particles without fluorochromes;
   (d) separating scattered light from fluorescence light;
   (e) detecting light emitted from the interaction of the particles with the light pulses and producing a second electrical signal in response thereto;
   (f) receiving and storing the first electrical signal and the second electrical signal; whereby the commencement time for the first electrical signal corresponding to a second electrical signal from the detection of scattered light from particles without fluorochromes and the commencement time for the first electrical signal corresponding to a second electrical signal from the fluorescence of fluorochrome-containing particles are used to correct the commencement time of the second electrical signal for fluorescence from fluorochrome-containing particles; and
   (g) determining the response function for said step of detecting scattered light emitted from the interaction of the particles with the light pulses; whereby the time-resolved fluorescence decay may be extracted by deconvoluting the response function for the fluorescence emission of the fluorochrome-containing particles.

13. The method for measuring time-resolved fluorescence decay for flowing particles containing a plurality of fluorochromes as described in claim 12, wherein the flow of particles includes hydrodynamically focused particle flow.

14. The method for measuring time-resolved fluorescence decay for flowing particles containing a plurality of fluorochromes as described in claim 13, wherein the hydrodynamically focused particle flow is provided by a flow cytometer.

15. The method for measuring time-resolved fluorescence decay for flowing particles containing a plurality of fluorochromes as described in claim 12, wherein said step of generating a train of light pulses is performed using a light source selected from the group consisting of electrooptic modulated cw lasers and acoustooptic modulated cw lasers.

16. The method for measuring time-resolved fluorescence decay for flowing particles containing a plurality of fluorochromes as described in claim 12, wherein the fluorescent light is separated from the scattered light using optical filters.

17. The method for measuring time-resolved fluorescence decay for flowing particles containing a plurality of fluorochromes as described in claim 12, wherein the light pulses having a known temporal relationship therebetween are equally spaced in time.

18. The method for measuring time-resolved fluorescence decay for flowing particles containing a plurality of fluorochromes as described in claim 17, wherein the light pulses having a known temporal relationship therebetween have a chosen pulse repetition rate and pulsewidth.

19. The method for measuring time-resolved fluorescence decay for flowing particles containing a plurality of fluorochromes as described in claim 18, wherein the light pulses having a known temporal relationship therebetween have a pulse repetition rate such that the time between pulses is at least three times longer than the fluorescence decay lifetime of the fluorochrome-containing particles.

20. The method for measuring time-resolved fluorescence decay for flowing particles containing a plurality of fluorochromes as described in claim 12, wherein said step of receiving and storing the first electrical signal and the second electrical signal is achieved using a digital storage oscilloscope.

21. A method for measuring time-resolved fluorescence decay for flowing particles containing a plurality of fluorochromes, which comprises the steps of:
(a) generating a train of light pulses having a known temporal relationship therebetween, each of the light pulses having a wavelength suitable for exciting particles containing fluorochromes;
(b) providing a flow of particles through the train of light pulses, whereby individual particles may interact with the light pulses producing fluorescence light for particles containing fluorochromes and scattered light for particles without fluorochromes;
(c) measuring the fluorescence response from individual particles containing fluorochromes;
(d) measuring the scattering response from individual particles without fluorochromes, whereby the response function for said step of measuring the fluorescence response from individual particles containing fluorochromes may be determined;
(e) measuring the apparent time shift between the light pulses which gave rise to the fluorescence response from the individual particles containing fluorochromes and the scattering response from the individual particles without fluorochromes;
(f) shifting the measured fluorescence response relative to the measured scattering response by the apparent time shift; and
(g) deconvoluting the time-resolved fluorescence decay form the fluorescence response of the fluorochrome-containing particles and the response function.

* * * * *